US008049884B2

(12) United States Patent
Tsukuda

(10) Patent No.: US 8,049,884 B2
(45) Date of Patent: Nov. 1, 2011

(54) SPECTROPHOTOMETER

(75) Inventor: Yasuo Tsukuda, Osaka (JP)

(73) Assignee: Shimadzu Corporation, Kyoto (JP)

( * ) Notice: Subject to any disclaimer, the term of this patent is extended or adjusted under 35 U.S.C. 154(b) by 178 days.

(21) Appl. No.: 12/444,308

(22) PCT Filed: Sep. 27, 2007

(86) PCT No.: PCT/JP2007/001048
§ 371 (c)(1),
(2), (4) Date: Apr. 3, 2009

(87) PCT Pub. No.: WO2008/044329
PCT Pub. Date: Apr. 17, 2008

(65) Prior Publication Data
US 2010/0045980 A1 Feb. 25, 2010

(30) Foreign Application Priority Data

Oct. 6, 2006 (JP) .................. 2006-274693

(51) Int. Cl.
*G01J 3/02* (2006.01)
*G01J 3/28* (2006.01)
*G01N 21/27* (2006.01)

(52) U.S. Cl. ........ 356/326; 356/244; 356/440; 356/319; 356/246

(58) Field of Classification Search .................. 356/246, 356/319, 440
See application file for complete search history.

(56) References Cited

U.S. PATENT DOCUMENTS

| | | | | |
|---|---|---|---|---|
| 7,365,852 B2 * | 4/2008 | Schleifer | ....................... | 356/440 |
| 7,375,815 B2 * | 5/2008 | Kralik | ........................... | 356/440 |

FOREIGN PATENT DOCUMENTS

| | | | |
|---|---|---|---|
| JP | 49-027485 U | | 3/1974 |
| JP | 05-052749 A | | 3/1993 |
| JP | 05-302893 A | | 11/1993 |
| JP | 05-315324 A | | 11/1993 |
| JP | 11-148896 A | | 6/1999 |
| JP | 2003-307408 | * | 10/2003 |
| JP | 2006-023088 A | | 1/2006 |
| JP | 2009-036664 A | | 2/2009 |

OTHER PUBLICATIONS

Written Opinion of the International Searching Authority dated Oct. 30, 2007, issued in corresponding International application No. PCT/JP2007/001048.

* cited by examiner

*Primary Examiner* — F. L. Evans
(74) *Attorney, Agent, or Firm* — Sughrue Mion, PLLC

(57) ABSTRACT

A liquid sample is dropped onto the upper surface of a transparent and cylindrical light-transmitting body (22), and the liquid sample is maintained as a droplet by the surface tension. From above the liquid sample, a transparent cover plate (25) is lowered down to the position where the lower surface thereof touches a spacer (23) in order that the liquid sample is held in the small gap formed between the upper surface of the light-transmitting body (22) and the lower surface of the transparent cover plate (25). A measurement light is provided into the liquid sample held in this manner from immediately above it, and passes through the liquid sample. The transmitted light emitted downwards through the light-transmitting body (22) is introduced into a spectro-detecting unit to be spectro-measured. The measurement optical path length can be adjusted by the height of the spacer (23). This enables an easy transmission spectro-measurement of an extremely small amount of liquid sample.

8 Claims, 5 Drawing Sheets

SPECTROPHOTOMETER

TECHNICAL FIELD

The present invention relates to a spectrophotometer for delivering light onto or into a liquid sample and measuring the transmitted light. More precisely, it relates to a spectrophotometer suitable for measuring the transmission characteristics of a small amount of liquid sample.

BACKGROUND ART

A conventional spectrophotometer such as an ultraviolet visible spectrophotometer which has been widely and generally used includes an optical system. In the optical system, for example, a light emitted from a light source is wavelength-dispersed by a spectroscope, a measurement light having a specific wavelength is taken out, the measurement light is delivered onto or into the sample placed in a sample chamber, and the light which has passed through the sample is detected. In the sample chamber, various types of sample cells and sample change mechanisms are placed in accordance with the purpose of analysis, the kind of sample, and other factors (for example, refer to Patent Document 1 or other documents). For example, in the measurement of the liquid sample's transmission characteristics such as transmissivity and absorbance, a polygonal or cylindrical cuvette cell for holding a liquid sample is generally used. The interior volume of a general cuvette cell is more than a few mL and it is required to prepare a sufficient quantity of liquid sample to fill the cuvette cell.

In recent years, an ultraviolet visible spectrophotometer as previously described has been used in the field of biochemistry, such as quantifying protein and DNA. In such cases, the quantity of the liquid sample to be analyzed is usually extremely small. In particular, in a DNA-related analysis, a sample is precious and expensive. In some cases, it is necessary to perform an analysis with a liquid sample of less than a few μL. A cuvette cell as previously described cannot be used for the purpose of analyzing such a small amount of liquid sample. In this connection, a container suitable for spectro-analyzing such a small amount of liquid sample is conventionally known.

Patent Document 2 or other documents for example disclose a sample cell for measuring a trace liquid sample. This is a capillary cell which siphons and holds a liquid sample by using a capillary action. However, even such a capillary cell generally requires a liquid amount of more than a few μL and a liquid sample less than this amount cannot be analyzed. In addition, a capillary cell has disadvantages in that injecting a liquid sample into the cell is cumbersome and cleaning after a measurement is troublesome.

On the other hand, as an apparatus capable of spectro-analyzing an extremely small amount (approximately 1 μL) of liquid sample, a spectrophotometer ND-1000 which is sold by NanoDrop Technologies Inc. in the United States is recognized (refer to Non-Patent Document 1). The schematic configuration of the sample holding unit in this spectrophotometer is illustrated in FIG. 9. In the sample holding unit, the downward end face of a light-delivering optical fiber 41 held by an upper base 40 and the upward end face of a light-receiving optical fiber 43 held by a lower base 42 are placed in such a manner as to face each other in the vertical direction. The lower base 42 is immobile, whereas the upper base 40 is vertically movable.

In placing a liquid sample, the upper base 40 is moved upwards for example and the liquid sample is dropped onto the upward end of the light-receiving optical fiber 43. After that, the upper base 40 is moved once downwards to the position where the downward end face of the light-delivering optical fiber 41 almost touches the upward end face of the light-receiving optical fiber 43 (refer to FIG. 9(a)). Then, the upper base 40 is drawn up to a predetermined position. This makes the liquid sample S vertically bridge the space between the downward end face of the light-delivering optical fiber 41 and the upward end face of the light-receiving optical fiber 43, forming a catenoid shape due to the surface tension, as illustrated in FIG. 9(b).

In this state, the liquid sample S between the light-delivering optical fiber 41 and the light-receiving optical fiber 43 can serve as an optical connector. Accordingly, the measurement light which has been delivered through the light-delivering optical fiber 41 passes through the liquid sample S to be sent into the light-receiving optical fiber 43. Generally, the optical path length in a liquid sample is set to be approximately 1 mm, and a very small amount (i.e. approximately 1 through 2 μL) of liquid sample can be analyzed.

However, this spectrophotometer has a disadvantage in that a light quantity loss occurs unless the optical axis of the light-delivering optical fiber 41 is coincident with that of the light-receiving optical fiber 43. Hence, the accuracy of the mechanism for vertically moving the upper base 40 and the positional accuracy of both the bases 40 and 42 are required to be sufficiently high, which increases the cost by that much. In addition, since the optical fibers 41 and 43 constituting the measurement optical system directly contact with the liquid sample S, the sample change operation is far more troublesome and time-consuming compared to the case, for example, of inserting a sample cell in a measurement light path in a sample chamber space or the like as previously described. Above all, it takes time to perform the measurement of a great number of samples while automatically changing the samples.

[Patent Document 1] Japanese Unexamined Patent Application Publication No. H05-315324

[Patent Document 2] Japanese Unexamined Patent Application Publication No. H05-302893

[Non-Patent Document 1] "NanoDrop ND-1000 Overview," [online], NanoDrop Technologies Inc., [Sep. 25, 2006], internet <URL: http://www.nanodrop.com/nd-1000-overview.html>

DISCLOSURE OF THE INVENTION

Problems to be Solved by the Invention

The present invention has been developed in view of the aforementioned problems, and the objective thereof is to provide a simple and inexpensive spectrophotometer for measuring a trace liquid sample, capable of performing a transmission measurement of an extremely small amount (approximately 1 through 2 μL or less) of liquid sample with a simple operation.

Means for Solving the Problems

To solve the previously described problems, the present invention provides a spectrophotometer for measuring a transmission characteristic of a liquid sample, including: an optical system for vertically forming a transmission path of a measurement light in an open space; and a sample holding unit, which is inserted in the transmission path of a measurement light formed by the optical system, for holding a liquid sample, wherein the sample holding unit includes:

a) a sample stage which is made of a light-transmitting material and whose upper surface and lower surface are both horizontal; and b) a window plate which is made of a light-transmitting material and can be held above the sample stage and on the liquid sample dropped onto the upper surface of the sample stage, in such a manner that a boundary face parallel to the upper surface is formed at a predetermined distance from the upper surface, and thereby allows a measurement to be performed by:

bringing the lower surface of the window plate and the upper surface of the sample stage closer to each other to reach the predetermined distance after the liquid sample is dropped onto the upper surface of the sample stage; and with the liquid sample touching the upper surface of the sample stage and the lower surface of the window plate, delivering a measurement light from above or below the liquid sample and measuring a light which has passed through the liquid sample downwards or upwards.

The sample stage and the window plate are preferably made of a material as transparent as possible. In particular, the sample stage is required to be hard enough to resist deformation by the weight of the liquid sample's droplet since the liquid sample is directly dropped onto the upper surface of the sample stage. Given these factors, silica glass may preferably be used as the material. Concretely speaking, a glass or plastic optical fiber may be cut into an appropriate length to be used as the sample stage.

In setting a liquid sample on the sample holding unit in the spectrophotometer according to the present invention, a small amount of liquid sample is dropped onto the upper surface of the sample stage by using a pipette or other instruments, with the window plate moved away from the space above the sample stage or with the window plate and the sample stage spaced to the extent of not causing an obstruction. The liquid sample dropped forms a droplet which is raised on the surface of the sample stage by the surface tension of liquid. After that, the window plate is lowered down to the position where the distance between the lower surface thereof and the upper surface of the sample stage is a predetermined distance. Then, the upper surface of the droplet touches the lower surface of the window plate, and the liquid sample is held in the space between the window plate's lower surface and the sample stage's upper surface. The upper surface forms the boundary phase between the liquid sample and the window plate, and the lower surface forms the boundary phase between the liquid sample and the sample stage. As just described, the window plate and the sample stage which sandwich the liquid sample from above and below are placed in the transmission path of a measurement light in the space. Therefore, the measurement light vertically (downwards or upwards) passes through the sample, and the predetermined distance forms the optical path length.

EFFECTS OF THE INVENTION

With the spectrophotometer according to the present invention, a liquid sample held in the sample holding unit can be a very small amount of approximately 1 through 2 μL or less than that. Therefore, it is preferable for the analysis of a trace liquid sample such as a biological sample. In addition, the preparation of the sample merely requires dropping a liquid sample onto the upper surface of the sample stage. Hence, the operation regarding the analysis is very simple and consumes little time. Furthermore, the portions touched by the liquid sample are flat: such as the upper surface of the sample stage, lower surface of the window plate or other portions. Therefore, it is easy to perform a cleaning operation by wiping and washing with cleaning fluid. Also, it is easily dryable.

Unlike the previously described configuration in which a liquid sample is held between the end surfaces of optical fibers, a liquid sample does not touch the main body of the apparatus such as a measurement optical system. Therefore, scratches and contaminations of the main body of the expensive apparatus can be prevented, which controls the maintenance cost. In addition, since the body of the optical system which constitutes the measurement optical path is not required to be displaced in setting or changing samples, the measurement optical path can be kept fixed, which is also effective in simplifying the structure and decreasing the cost. As a matter of course, adjusting operation of the optical axis between the light-delivering optical fiber and the light-receiving optical fiber is not necessary. Therefore, there is no risk of light quantity loss due to the disagreement of the optical axes. Furthermore, the sample change operation is easy either by manual or automatic operation, which enables the enhancement in the throughput of the analysis.

In the spectrophotometer according to the present invention, as previously described, the distance between the sample stage's upper surface and the window plate's lower surface forms the measurement optical path length. Therefore, the setting accuracy of the distance needs to be enhanced in order to perform an accurate measurement. Given this factor, as an embodiment of the present invention, the bodies of the sample stage and the window plate, or a member holding each of the sample stage and the window plate is made to touch a regulatory member disposed in the space between the sample stage and the window plate in order to set a distance between the upper surface of the sample stage and the lower surface of the window plate to be the predetermined distance.

In this configuration, after the liquid sample is dropped onto the upper surface of the sample stage, the distance between the window plate and the sample stage is gradually reduced. When the bodies of the sample stage and the window plate touch or the member that holds them touches the regulatory member, the narrowing operation is halted. In this manner, the aforementioned distance can be accurately set. This accomplishes an accurate determination of the measurement optical path length and the measurement accuracy is increased. Simultaneously, the configuration is simple and a high positional accuracy is not required in the stopping operation of the moving mechanism for the window plate for example. Therefore, this configuration is also advantageous in reducing the cost.

Generally, in a transmission measurement, the measurement accuracy can be increased, for example, by decreasing the measurement optical path length if the sample has a high concentration and hence a large absorbance per unit length or increasing the measurement optical path length if the sample has a low concentration and hence a small absorbance per unit length. Given these factors, in the configuration of the aforementioned embodiment, the regulatory member may be changed in height in order to change the predetermined distance. With this configuration, the measurement optical path length can be easily changed. Regardless of such a change, the completely same measurement optical system can be used and a plurality of sample cells having different optical path lengths are not required as with a cuvette cell. Consequently, it is possible to realize the change of the measurement optical path length with a small increase in cost.

BRIEF DESCRIPTION OF THE DRAWINGS

FIG. 8(b) is an end view of the same pedestal unit viewed from the arrow A-A'.

EXPLANATION OF NUMERALS

1 . . . Light Emission Unit
2 . . . Light Source
3 . . . Mirror
4 . . . Lens
5 . . . Sample Chamber
6 . . . Cover Plate Holder
7 . . . Vertical Movement Drive Unit
8 . . . Pedestal Holder
9 . . . Rotary Plate
10 . . . Shaft
11 . . . Detection Unit
12 . . . Lens
13 . . . Slit
14 . . . Diffraction Grating
15 . . . Detector
20 . . . Pedestal Unit
21 . . . Base Plate
22 . . . Light Transmitting Body
23 . . . Spacer
24,24a through 24d . . . Auxiliary Spacer
25 . . . Transparent Cover Plate
26 . . . Pipette
27 . . . Hem
30 . . . Controller
31 . . . Photometer Unit
32 . . . Signal Processor
33 . . . Output Unit
34 . . . Sample Holding Drive Unit
35 . . . Wiping Mechanism Drive Unit
36 . . . Operation Unit

BEST MODE FOR CARRYING OUT THE INVENTION

Figure 1:
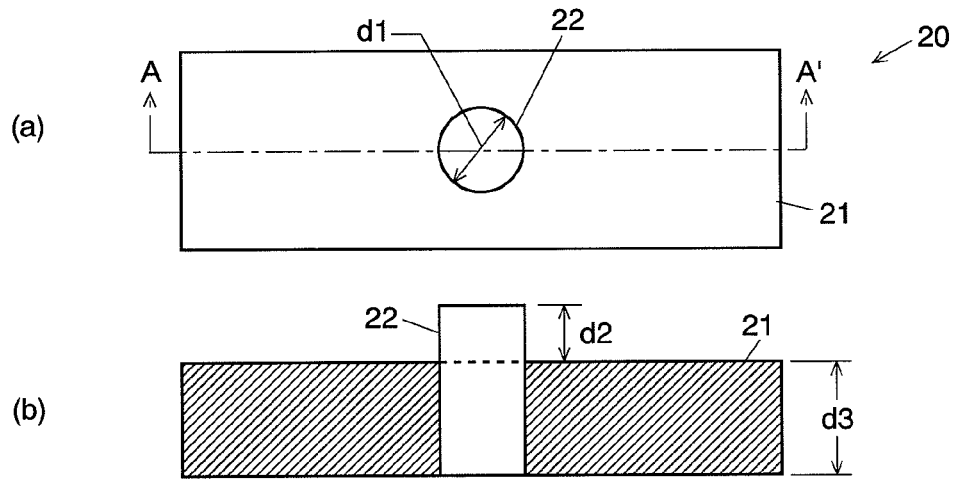
FIG. 1(a) is a top plain view of a pedestal unit of the sample holding unit which is used in the spectrophotometer of an embodiment of the present invention.
FIG. 1(b) is an end view of the same pedestal unit viewed from the arrow A-A'.
Figure 2:
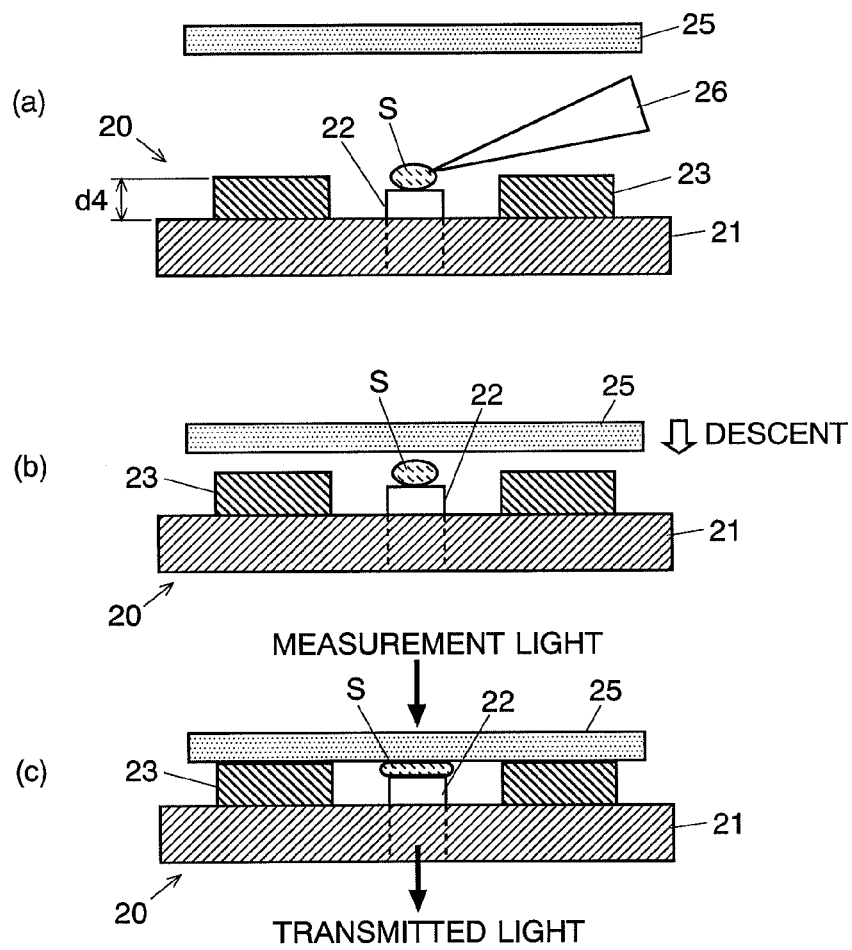
FIG. 2 is a schematic side view for explaining a procedure of setting a liquid sample in the sample holding unit illustrated in FIG. 1.

An embodiment of the spectrophotometer according to the present invention will be described with reference to the figures. First, the characteristic configuration of the sample holding unit which is used in the spectrophotometer of the present embodiment is described. FIG. 1(a) is a top plain view of the pedestal unit of the sample holding unit and FIG. 1(b) is an end view of the same pedestal unit viewed from the arrow A-A'. FIG. 2 is a schematic side view for explaining the procedure of setting a liquid sample in this sample holding unit.

The sample holding unit is roughly composed of a pedestal unit 20 and a transparent cover plate (i.e. the window plate in the present invention) 25 to be placed thereon. As illustrated in FIG. 1, the pedestal unit 20 is composed of a base plate 21 made of a material such as metal or plastic having a light-blocking property and a cylindrical light-transmitting body (i.e. the sample stage in the present invention) 22 made of a material having a transparent property. The light-transmitting body 22 is fitted into a circular hole vertically bored through the base plate 21. The flat lower surface of the light-transmitting body 22 is approximately level with the lower surface of the base plate 21, whereas the flat upper surface of the light-transmitting body 22 is projected upwards by the height d2 with respect to the upper surface of the base plate 21. In this example, the plate thickness d3 of the base plate 21 is 2 mm, and the diameter d1 of the light-transmitting body 22 is 0.8 through 1.0 mm. The diameter d1 is considered so that a liquid sample can remain as a droplet on the surface of the light-transmitting body 22.

Since a liquid sample is directly dropped onto the upper surface of the light-transmitting body 22, the light-transmitting body 22 must be hard enough to resist deformation by the weight of the droplet. Furthermore, it should preferably have a high transparent property. For example, silica glass can be used, and plastic is also allowable. As the light-transmitting body 22, an optical fiber (or optical fiber wire) cut into an appropriate length can be used. Likewise, the transparent cover plate 25 may be made of silica glass, plastic, or similar material. In addition, the upper surface (i.e. wetted surface) and lower surface of the light-transmitting body 22 may preferably be optically polished in order to reduce the scattering of light and increase the surface tension on the wetted surface. The upper surface of the light-transmitting body 22 may preferably be water-repellent finished in order that a liquid sample does not spread but gathers into a droplet.

In setting a liquid sample on the sample holding unit which has the aforementioned configuration, as illustrated in FIG. 2(a), spacers (the regulatory member in the present invention) 23 with the height d4 which is appropriately larger than the aforementioned height d2 are placed on the upper surface of the base plate 21. With the transparent cover plate 25 raised to a position where it does not cause an obstruction or removed from the space above the pedestal unit 20, a small amount of liquid sample S is dropped onto the upper surface of the light-transmitting body 22 by using a pipette 26 or other instruments. The liquid sample S dropped becomes a droplet on the upper surface of the light-transmitting body 22 by the surface tension.

The liquid sample S is covered by the transparent cover plate 25 from above as illustrated in FIG. 2(b). The transparent cover plate 25 is lowered down until the lower surface thereof touches the upper surface of the spacers 23. Since the height d4 of the spacers 23 is larger than that of the projection height d2 of the light-transmitting body 22 as previously described, the gap with the distance of d4-d2 is formed between the lower surface of the transparent cover plate 25 and the upper surface of the light-transmitting body 22. The liquid sample S is held in such a manner as to fill the gap (refer to FIG. 2(c)). In other words, the liquid sample S is sandwiched by the transparent cover plate 25 and the light-transmitting body 22, and the lower surface of the transparent cover plate 25 forms the upper boundary phase of the liquid sample S and the upper surface of the light-transmitting body 22 forms the lower boundary phase of the liquid sample S. That is the method of setting a liquid sample in the sample holding unit.

In measuring the transmission characteristics such as transmissivity and absorbance of the liquid sample S prepared in the manner as just described, a measurement light is delivered vertically downwards from above to the liquid sample S. The optical axis of the measurement light is set to proceed approximately along the central axis of the cylindrical light body 22, and a transmitted light which has passed through the liquid sample S filled between the transparent cover plate 25 and the light-transmitting body 22 passes directly downwards. Accordingly, the distance of d4-d2 forms the optical path length L1 of the measurement of the liquid sample S (refer to FIG. 3(a)), and the optical path length is uniquely and accurately determined independently from the amount of the liquid sample which has been initially dropped.

Figure 3:
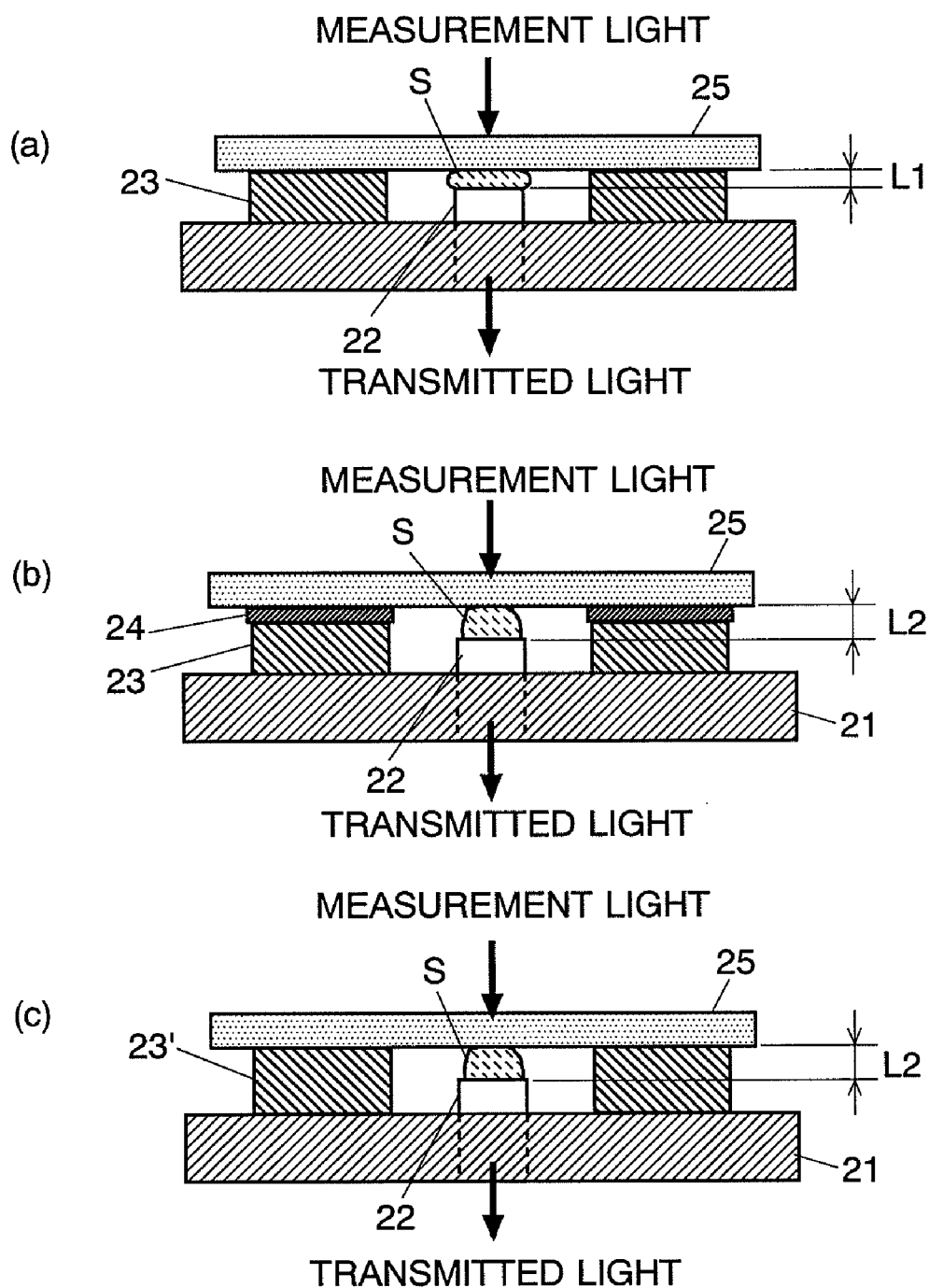
FIG. 3 is a schematic side view illustrating a configuration for changing the measurement optical path length in the sample holding unit illustrated in FIG. 1.

Since the measurement optical path length depends on the height d4 of the spacers 23 as just described, the measurement optical path length can be easily changed by replacing the spacers 23 with spacers 23' having a different height, as illustrated in FIG. 3(c) for example. In the example of FIG. 3(c), the optical path length is increased to L2. Alternatively, in place of replacing the spacers 23, another auxiliary spacers 24 may be inserted on the spacers 23 as illustrated in FIG. 3(b) to change the overall height. Generally, the measurement optical path length may be changed for a sample whose concentration is different. However, the optical path length is not required to be changed in a stepless manner, but only a few steps for changing are sufficient. Therefore, even in the method of using spacers having different heights, it is not necessary to prepare a large number of spacers. Meanwhile, in the case where the amount of the liquid sample is 1 through 2 μL, the appropriate optical path length is within the range approximately between 0.2 and 0.7 mm.

Figure 4:
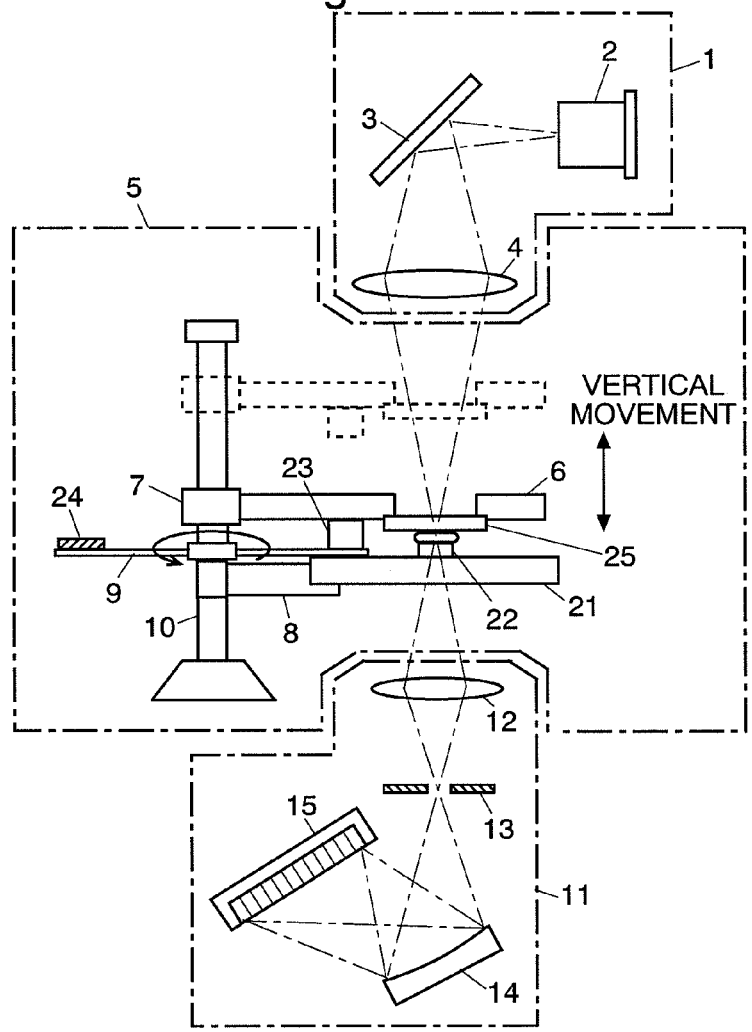
FIG. 4 is an overall configuration diagram of the optical system of the spectrophotometer of the present embodiment.
Figure 5:
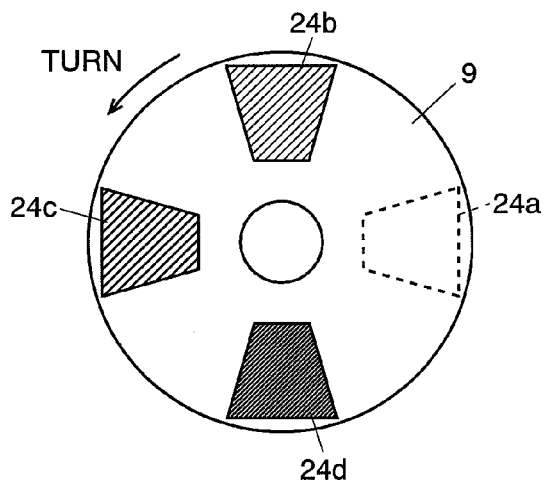
FIG. 5 is a plain view of a rotary plate for changing the measurement optical path length viewed from above.

Next, an embodiment of the spectrophotometer for measuring the transmission characteristic of a liquid sample using the sample holding unit will be explained with reference to FIGS. 4 and 5. FIG. 4 is an overall configuration diagram of the optical system of the spectrophotometer of the present embodiment.

In this spectrophotometer, a measurement light is emitted vertically downwards from the light emission unit 1. A detection unit 11 for spectro-detecting the transmitted light which has passed through the sample is placed under the light emission unit 1 across a sample chamber 5. That is, in this optical system, a measurement light proceeds downwards from above in the open space in which the sample chamber 5 is placed. Concretely speaking, in the light emission unit 1, a light emitted from the light source 2 is reflected by the mirror 3 and the traveling direction is changed downwards, and the light is converged by the lens 4 and delivered as the measurement light from approximately immediately above to the liquid sample S which is held in the sample holding unit. As previously described, the liquid sample S is held between the transparent cover plate 25 and the light-transmitting body 22. The position of the pedestal unit 20 is fixed with respect to a shaft 10 by a pedestal holder 8. On the other hand, the transparent cover plate 25 is held by a cover plate holder 6 and can be vertically moved along the shaft 10 by a vertical movement drive unit 7.

In addition, on a discoid rotary plate 9 which can freely turn around the shaft 10, a plurality of auxiliary spacers 24 having different heights are mounted at intervals from each other in a circumferential direction. FIG. 5 is a plain view of the rotary plate 9 viewed from above. By turning the rotation plate 9 around the shaft 10, one of the auxiliary spacers 24a through 24d having a desired height is inserted on the base plate 21. However, for the auxiliary spacer 24a, only the thickness of the body of the rotary plate 9 functions as an auxiliary spacer. In this example, the spacer 23 is attached not on the pedestal unit 20 but on the lower surface of the cover plate holder 6. When the cover plate holder 6 descends, the lower surface of the spacer 23 touches the upper surface of the base plate 21 or the auxiliary spacer 24 which is inserted in the gap in between.

With the transparent cover plate 25 raised, a liquid sample to be analyzed is dropped onto the upper surface of the light-transmitting body 22 of the sample holding unit as previously described, and after that, the cover plate holder 6 is lowered down by the vertical movement drive unit 7. Then, the lower surface of the spacer 23 touches one of the auxiliary spacers 24a through 24d which is located on the base plate 21, and the descent of the cover plate holder 6, i.e. the transparent cover plate 25, is halted at the position. Consequently, the liquid sample S is held between the transparent cover plate 25 and the light-transmitting body 22, and the measurement optical path length is determined in accordance with the auxiliary spacers 24a through 24d.

For the liquid sample S which has been prepared in the manner as just described, a measurement light is delivered from immediately above through the transparent cover plate 25 as illustrated in FIG. 4. In the course of passing through the liquid sample S, the wavelength components in accordance with the components of the sample S are absorbed, and a transmitted light is emitted downwards by way of the light-transmitting body 22. Many unnecessary lights such as a scattered light are blocked by the base plate 21 which has a light-blocking property and are not emitted downwards. The transmitted light is converged by the lens 12 in the detection unit 11, and the area of light is limited by a slit 13. After that, the transmitted light is introduced into a diffraction grating 14. In the diffraction grating 14, the transmitted light is wavelength-dispersed and the wavelength-dispersed lights are virtually simultaneously detected by a multichannel detector 15 such as a charge-coupled device (CCD) linear sensor. Of course, the configuration of the optical system can be appropriately changed: for example, the diffraction grating 14 may be rotated to scan the wavelengths of the light falling onto the detector 15. Alternatively, a double beam configuration may be used.

As previously described, a detection signal reflecting the transmission characteristic of the liquid sample S can be obtained in the detector 15. Therefore, in the signal processor, which will be described later, an absorption spectrum of a predetermined wavelength range for example can be created.

As is clearly illustrated in FIG. 4, the sample holding unit composed of the transparent cover plate 25 and the pedestal unit 20 can be easily replaced without affecting the measurement optical system such as the light emission unit 1 and the detector unit 11, since it is placed in the open space (in the sample chamber 5 in FIG. 4) in which a measurement light passes. Hence, samples to be measured can be changed one after another. In the replacement operation, only the pedestal unit 20 may be replaced, or the pair consisting of the pedestal unit 20 and the transparent cover plate 25 may be replaced. In the case where only the pedestal unit 20 is replaced and the transparent cover plate 25 is kept unchanged, the lower surface of the transparent cover plate 25 which is touched by a liquid sample is required to be cleaned (or wiped) to prevent contamination. However, in any case, an automatic change of samples can be realized by adding a simple mechanism.

Figure 6:
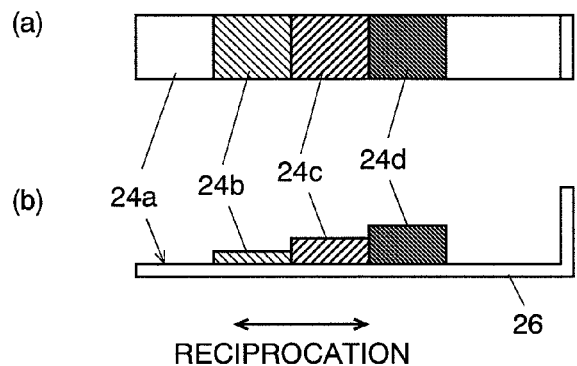
FIG. 6(a) is a top view of another configuration for changing the measurement optical path length.
FIG. 6(b) is an elevational view of the same configuration.

Although the auxiliary spacers 24a through 24d can be appropriately selected in accordance with the sample concentration, in place of the turning-type changing mechanism as previously described, a mechanism as illustrated in FIG. 6 can be used to easily change the measurement optical path length in a similar manner. In this configuration, the auxiliary spacers 24*a* through 24*d* with different thicknesses are linearly aligned and they can be reciprocated along the alignment direction.

Figure 7:
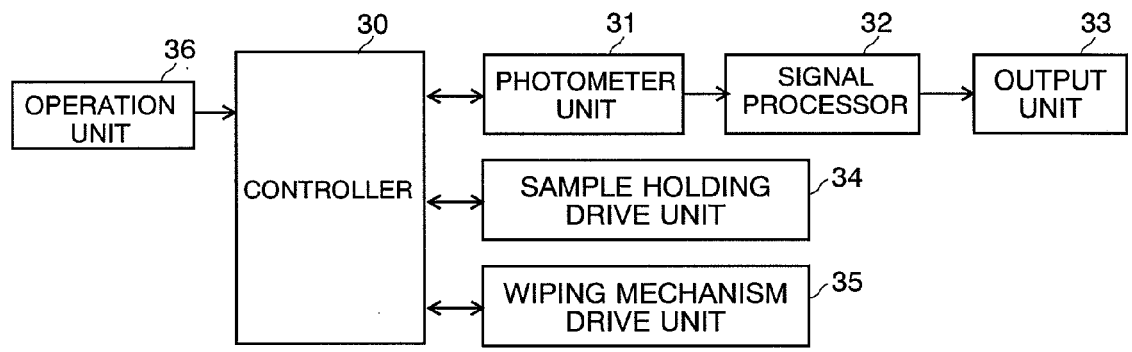
FIG. 7 is a block diagram of the control system of the spectrophotometer based on the optical system illustrated in FIG. 4.

FIG. 7 is a block diagram of the control system of the spectrophotometer based on the optical system illustrated in FIG. 4. In this spectrophotometer, a variety of operations other than dropping a sample are automated in order to efficiently perform the measurement of the sample. A controller 30 which includes a microcomputer and other units controls, in accordance with a predetermined sequence, a sample holding drive unit 34 for driving a motor or other units included in the vertical movement drive unit 7 for vertically moving the transparent cover plate 25, a wiping mechanism drive unit 35 for driving a mechanism for wiping an after-measured liquid sample attached on the lower surface of the transparent cover plate 25 and the upper surface of the light-transmitting body 22, and a photometer unit 31 including the light emission unit 1 and the detection unit 11. The operation unit 36 connected to the controller 30 is for providing instructions such as starting a measurement or a temporary halt. The detection signal obtained in the photometer unit 31 is processed in the signal processor 32, and an absorption spectrum and other reports are created. The result of the processing is provided from the output unit 33.

When the present apparatus is in the state of waiting for a measurement (i.e. standby state), the transparent cover plate 25 is kept raised. In this state, a person in charge of the analysis drops a small amount of liquid sample onto the upper surface of the light-transmitting body 22 with a micropipette and indicates the start of the measurement through the operation unit 36. Then, the controller 30 which has received this instruction operates the sample holding drive unit 34 to descend the transparent cover plate 25 to a predetermined height. Consequently, the liquid sample is held between the light-transmitting body 22 and the transparent cover plate 25 as previously described. Next, the controller 30 provides an instruction to the photometer unit 31 to deliver a measurement light into the liquid sample and the intensity of the transmitted light is measured. The wavelength range, wavelength steps, and other conditions in the measurement are determined based on the measurement conditions which have been set in advance. After the completion of the measurement, the transparent cover plate 25 is raised to a predetermined height by the sample holding drive unit 34. After that, a wiping head with a piece of waste cloth attached thereon is moved by the wiping mechanism drive unit 35 to remove a liquid sample from the upper surface of the light-transmitting body 22 and the lower surface of the transparent cover plate 25. Next, the wiping head is moved out from the space between the light-transmitting body 22 and the transparent cover plate 25, and with the transparent cover plate 25 raised to the highest point by the sample holding drive unit 34, the system is brought into a standby state, awaiting the instruction for the next measurement. As an example of the wiping mechanism, the mechanism proposed in Japanese Patent Application No. 2007-201876 or other documents by the applicant of the present invention can be used.

Figure 8:
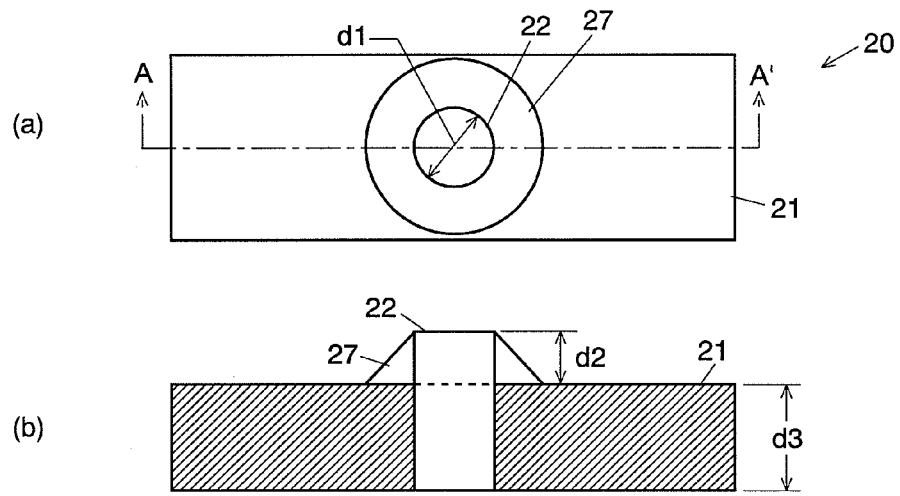
FIG. 8 is a top plain view of the pedestal unit of the sample holding unit in the spectrophotometer of another embodiment.
Figure 9:
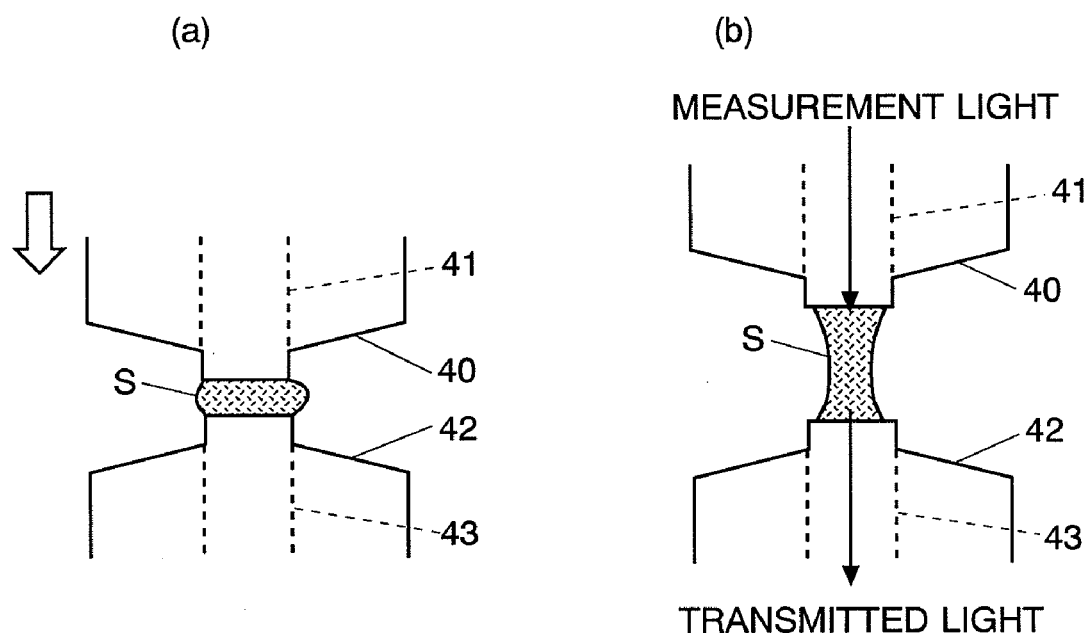
FIG. 9 is an explanation diagram for a conventional method of holding a trace liquid sample.

If the sample holding unit is configured as shown in FIG. 1, the waste cloth, which is made of a paper towel or the like, will easily get stuck in the corner of approximately 90° on the upper surface of the light-transmitting body 22 when it is in contact with the upper surface of the light-transmitting body 22 while being moved virtually horizontally in order to wipe the liquid sample remaining on the upper surface of the light-transmitting body 22, which may disturb the waste cloth's smooth movement and also fabrics of the waste cloth might remain. Given these factors, if the ease of wiping a liquid sample needs special consideration, the configuration of the sample holding unit may be modified as illustrated in FIG. 8. In FIG. 8, the same components illustrated in FIG. 1 are indicated with the same numerals. In the configuration of this modification example, a hem 27 whose surrounding face is conical is placed around the cylindrical light-transmitting body 22 which is projected upwards from the base plate 21. The light-transmitting body 22 and the hem 27 may either be united or separated. With this configuration, the waste cloth does not easily get stuck in the corner of the upper surface of the light-transmitting body 22. Therefore, the wiping head's smooth movement is assured, and simultaneously it is possible to prevent the fabrics of the waste cloth from sticking to the light-transmitting body 22.

In the previous explanation, the dropping of a liquid sample is not automated but performed by an operator. This is because it is generally difficult for inexpensive apparatuses to take and drop a liquid sample by an extremely small amount of approximately 1 μL or less using a micropipette. As a matter of course, this operation can also be automated.

It should be noted that the embodiment described thus far is merely an example of the present invention, and any modification, adjustment, or addition appropriately made within the spirit of the present invention is also covered by the claims of the present patent application.

The invention claimed is:

1. A spectrophotometer for measuring a transmission characteristic of a liquid sample, including: an optical system for vertically forming a tramsmission path of a measurement light in an open space; and a sample holding unit, which is inserted in the transmission path of a measurement light formed by the optical system, for holding a liquid sample, wherein the sample holding unit comprises:
   a) a sample stage which is composed of a base material and a light-transmitting body projected with respect to the base material and an upper surface and a lower surface of the light-transmitting body are both horizontal; and
   b) a window plate which is made of a light-transmitting material and can be held above the sample stage and on the liquid sample dropped onto the upper surface of the light-transmitting body, in such a manner that a boundary phase parallel to the upper surface is formed at a predetermined distance from the upper surface,
   and thereby allows a measurement to be performed by:
   bringing the lower surface of the window plate and the upper surface of the light-transmitting body closer to each other to reach the predetermined distance after the liquid sample is dropped onto the upper surface of the light-transmitting body; and
   with the liquid sample touching the upper surface of the light-transmitting body and the lower surface of the window plate, delivering a measurement light from above or below the liquid sample and measuring a light which has passed through the liquid sample downwards or upwards.

2. The spectrophotometer according to claim 1, wherein:
   a body of the sample stage and the window plate, or a member holding each of the sample stage and the window plate is made to touch a regulatory member disposed in a space between the sample stage and the window plate in order to set a distance between the upper surface of the light-transmitting body and the lower surface of the window plate to be the predetermined distance.

3. The spectrophotometer according to claim 2, wherein:
a height of the regulatory member can be changed to change the predetermined distance.

4. The spectrophotometer according to claim 1, further comprising:
a moving means for vertically moving at least either one of the window plate and the sample stage to change a distance between the lower surface of the window plate and the upper surface of the light-transmitting body; and
a light measurement means for delivering a measurement light, with the liquid sample touching the upper surface of the light-transmitting body and the lower surface of the window plate, from above or below the liquid sample and for measuring a light which has passed through the liquid sample downwards or upwards.

5. The spectrophotometer according to claim 4, further comprising:
a controller for controlling each of the moving means and the light measurement means in such a manner that at least either one of the window plate and the sample stage is moved in order to set the distance between the lower surface of the window plate and the upper surface of the light-transmitting body to be the predetermined distance by the moving means, and with the liquid sample touching the upper surface of the sample stage and the lower surface of the window plate, a measurement light is delivered from above or below the liquid sample and a light which has passed through the liquid sample downwards or upwards is measured by the light measurement means.

6. The spectrophotometer according to claim 2, further comprising:
a moving means for vertically moving at least either one of the window plate and the sample stage to change a distance between the lower surface of the window plate and the upper surface of the sample stage; and
a light measurement means for delivering a measurement light, with the liquid sample touching the upper surface of the light-transmitting body and the lower surface of the window plate, from above or below the liquid sample and for measuring a light which has passed through the liquid sample downwards or upwards.

7. The spectrophotometer according to claim 6, further comprising:
a controller for controlling each of the moving means and the light measurement means in such a manner that at least either one of the window plate and the sample stage is moved in order to set the distance between the lower surface of the window plate and the upper surface of the light-transmitting body to be the predetermined distance by the moving means, and with the liquid sample touching the upper surface of the light-transmitting body and the lower surface of the window plate, a measurement light is delivered from above or below the liquid sample and a light which has passed through the liquid sample downwards or upwards is measured by the light measurement means.

8. The spectrophotometer according to claim 1, wherein:
the light-transmitting body is cylindrical and the sample stage has: a hem having a conical surrounding face placed around the light-transmitting body.

* * * * *